(12) United States Patent
Yamaguchi et al.

(10) Patent No.: US 7,057,729 B2
(45) Date of Patent: Jun. 6, 2006

(54) PHOTOTHERMAL CONVERSION SPECTROSCOPIC ANALYSIS METHOD, AND PHOTOTHERMAL CONVERSION SPECTROSCOPIC ANALYSIS APPARATUS FOR CARRYING OUT THE METHOD

(75) Inventors: Jun Yamaguchi, Sagamihara (JP); Akihiko Hattori, Sagamihara (JP)

(73) Assignee: Nippon Sheet Glass Co., Ltd., Osaka (JP)

( * ) Notice: Subject to any disclaimer, the term of this patent is extended or adjusted under 35 U.S.C. 154(b) by 323 days.

(21) Appl. No.: 10/445,629

(22) Filed: May 27, 2003

(65) Prior Publication Data

US 2003/0223070 A1  Dec. 4, 2003

(30) Foreign Application Priority Data

May 30, 2002  (JP) .............................. 2002-157796

(51) Int. Cl.
  *G01N 21/00*  (2006.01)
(52) U.S. Cl. ...................................... 356/432; 356/442
(58) Field of Classification Search ................ 356/344, 356/432
  See application file for complete search history.

(56) References Cited

U.S. PATENT DOCUMENTS

| | | | | |
|---|---|---|---|---|
| 4,243,327 A | * | 1/1981 | Frosch et al. | 356/432 |
| 4,591,272 A | * | 5/1986 | Morris et al. | 356/432 |
| 4,938,593 A | * | 7/1990 | Morris et al. | 356/344 |
| 5,513,006 A | * | 4/1996 | Schulz et al. | 356/432 |
| 5,926,273 A | * | 7/1999 | Kimura et al. | 356/502 |

FOREIGN PATENT DOCUMENTS

| | | | |
|---|---|---|---|
| EP | 1251348 A1 | * | 8/2001 |
| JP | 63-63502 B2 | | 12/1988 |
| JP | 8-178897 A | | 7/1996 |
| JP | 10-232210 A | | 9/1998 |

OTHER PUBLICATIONS

Rojas et al, Thermal lens spectroscopy using a diode laser and optical fibers, American Institute of Physics, May 1992, pp. 2989-2993.*

* cited by examiner

*Primary Examiner*—Layla G. Lauchman
(74) *Attorney, Agent, or Firm*—Frishauf, Holtz, Goodman & Chick, P.C.

(57) ABSTRACT

There is provided that enables high-sensitivity analysis to be carried out, and a photothermal conversion spectroscopic analysis apparatus that is compact in size and is able to implement the photothermal conversion spectroscopic analysis method. Exciting light and detecting light are convergently irradiated onto the sample by a converging lens. The sample is analyzed using a change in intensity of the detecting light due to refraction upon passing through the thermal lens produced through the convergent irradiation of the exciting light. A molar absorption coefficient of the sample at a wavelength of the exciting light is a predetermined number of times greater than a molar absorption coefficient of the sample at a wavelength of the detecting light.

9 Claims, 7 Drawing Sheets

PHOTOTHERMAL CONVERSION SPECTROSCOPIC ANALYSIS METHOD, AND PHOTOTHERMAL CONVERSION SPECTROSCOPIC ANALYSIS APPARATUS FOR CARRYING OUT THE METHOD

BACKGROUND OF THE INVENTION

1. Field of the Invention

The present invention relates to a photothermal conversion spectroscopic analysis method and photothermal conversion spectroscopic analysis apparatus for analyzing a sample using detecting light that has passed through a thermal lens produced in the sample, and in particular to a photothermal conversion spectroscopic analysis method and photothermal conversion spectroscopic analysis apparatus that enable high-accuracy ultramicroanalysis to be carried out in a very small space.

2. Description of the Related Art

In recent years, spectroscopic analysis has come to be widely used as a method for carrying out analysis or measurement on semiconductors, biological samples, various types of liquid sample, and so on. However, with a conventional spectroscopic analysis method, in the case of analyzing a very small amount of a substance in a very small space, a vacuum environment is often required as a measurement condition, and there has been a problem that to realize such an environment the apparatus must be made large in size and the cost increases, and furthermore there has been a problem that the sample may be damaged or destroyed by an electron beam or ion beam used. Moreover, when handling an extremely small amount of a sample in a solution, biological tissue, or the like, it becomes essential to use an optical microscope, which enables high-accuracy analysis to be carried out with high spatial resolution. The only type of microscope actually used in this optical field is a laser fluorescence microscope, and hence the target of analysis is limited to being a laser fluorescence microscope fluorescent molecule, which is inconvenient.

Consequently, there have been demands for an analysis method according to which the target of analysis is not limited to being a fluorescent molecule, a vacuum environment is not required, analysis can be carried out without contacting or damaging the sample, and high-accuracy analysis can be carried out with high spatial resolution.

A photothermal conversion spectroscopic analysis method that uses a thermal lens effect brought about by photothermal conversion is attracting attention as an analysis method that satisfies these demands.

This photothermal conversion spectroscopic analysis method uses a photothermal conversion effect in which a solute in a solution absorbs convergently irradiated light and thus emits thermal energy, the temperature of the solvent is locally raised by this thermal energy and hence the refractive index of the solvent changes locally, and as a result a thermal lens is formed in the solvent.

Figure 4:
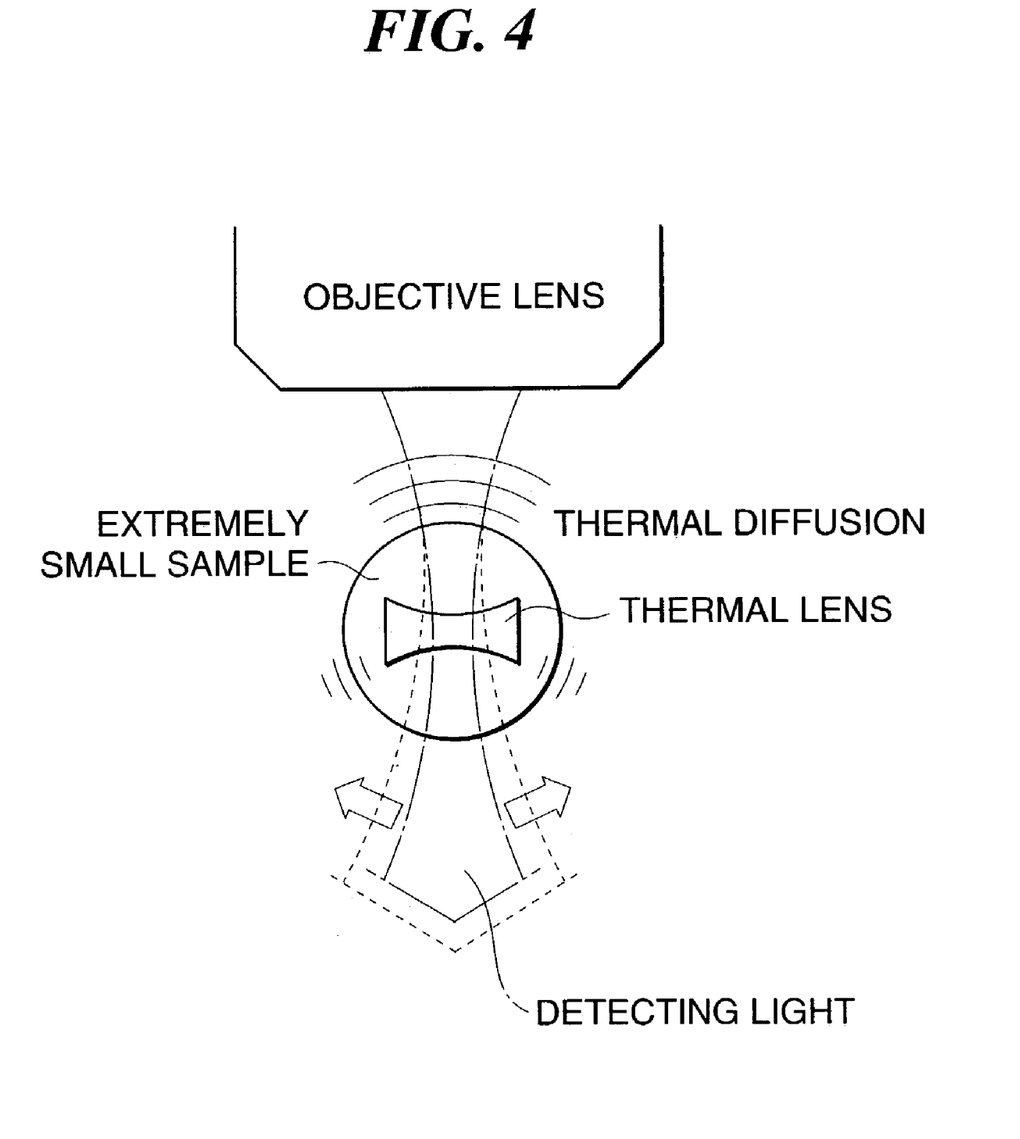
FIG. 4 is a view useful in explaining the principle of a thermal lens.

FIG. 4 is a view useful in explaining the principle of a thermal lens.

In FIG. 4, exciting light is convergently irradiated onto an extremely small sample via an objective lens, whereby a photothermal conversion effect is brought about. For most substances, the refractive index drops as the temperature rises, and hence in the sample onto which the exciting light has been convergently irradiated, the refractive index drops due to the rise in temperature in the vicinity of the center of the converged light. Due to thermal diffusion, the rise in temperature becomes smaller, and hence the drop in refractive index becomes smaller, with increasing distance from the center of the converged light. Optically, the resulting refractive index distribution produces exactly the same effect as a concave lens, and hence the effect is referred to as the thermal lens effect. The degree of the thermal lens effect, which corresponds to the power of the concave lens, is proportional to the optical absorbance of the sample. Moreover, in the case that the refractive index increases with temperature, a similar effect is produced, but the thermal lens is convex.

In the photothermal conversion spectroscopic analysis method described above, thermal diffusion, i.e. change in refractive index, is measured, and hence the method is suitable for detecting concentrations in extremely small samples.

A photothermal conversion spectroscopic analysis apparatus that carries out the photothermal conversion spectroscopic analysis method described above is disclosed, for example, in Japanese Laid-open Patent Publication (Kokai) No. 10-232210.

In such a photothermal conversion spectroscopic analysis apparatus, the sample is disposed below the objective lens of a microscope, and exciting light of a predetermined wavelength outputted from an exciting light source is introduced into the microscope, whereby the exciting light is convergently irradiated via the objective lens onto an extremely small region in the sample. A thermal lens is thus formed, with the center of the thermal lens being at the center of the converged light.

Moreover, detecting light that is outputted from a detecting light source and has a wavelength different to the exciting light passes through the microscope and is thus convergently irradiated onto the thermal lens, whereby the detecting light passes through the thermal lens in the sample and is thus diverged or converged. The diverged or converged detecting light exiting from the sample is taken as signal light, and is passed through a converging lens and a filter or through just a filter, before being detected by a detector. The intensity of the detected signal light depends on the power of the thermal lens formed in the sample.

The detecting light may have the same wavelength as the exciting light, or the exciting light may also be used as the detecting light. However, in general better sensitivity is obtained in the case that the exciting light and the detecting light have different wavelengths to one another.

However, before now studies had not been carried out into how the wavelengths of the exciting light and the detecting light should be selected to enable high-sensitivity measurement to be carried out.

Moreover, in the conventional photothermal conversion spectroscopic analysis apparatus described above, the optical system for the light sources, the measurement part and the detection part (photoelectric conversion part) is complex in arrangement and/or construction, and hence the apparatus is large in size and portability is poor. There has thus been a problem that when carrying out analysis or a chemical reaction using the photothermal conversion spectroscopic analysis apparatus, there are limitations with regard to the installation site and the operation of the photothermal conversion spectroscopic analysis apparatus.

Moreover, in the conventional photothermal conversion spectroscopic analysis apparatus described above, the exciting light and the detecting light are led to the sample through open space, and hence various optical system components such as the light sources, mirrors and lenses must be fixed onto a sturdy baseplate so that these components do not move during measurement. Furthermore, the optical axes of the exciting light and the detecting light may shift out of alignment upon changes in the installation environment of the photothermal conversion spectroscopic analysis apparatus such as temperature, and hence jigs for adjusting for such shifts are required. These jigs are also a cause of the photothermal conversion spectroscopic analysis apparatus becoming larger in size and the portability worsening.

Figure 5A:
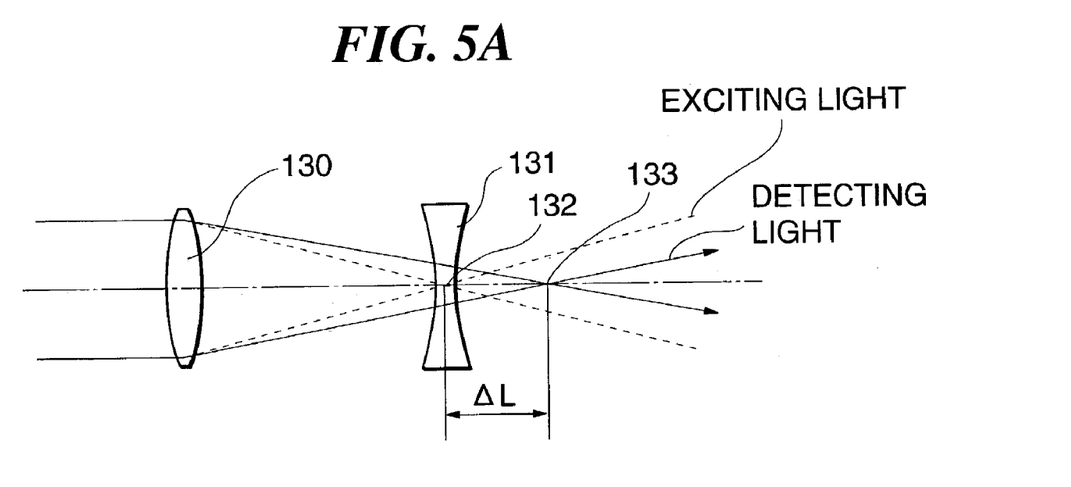
FIG. 5A is a view useful in explaining the formation position of a thermal lens formed by exciting light and the focal position of detecting light in the case that an objective lens has chromatic aberration.
Figure 5B:
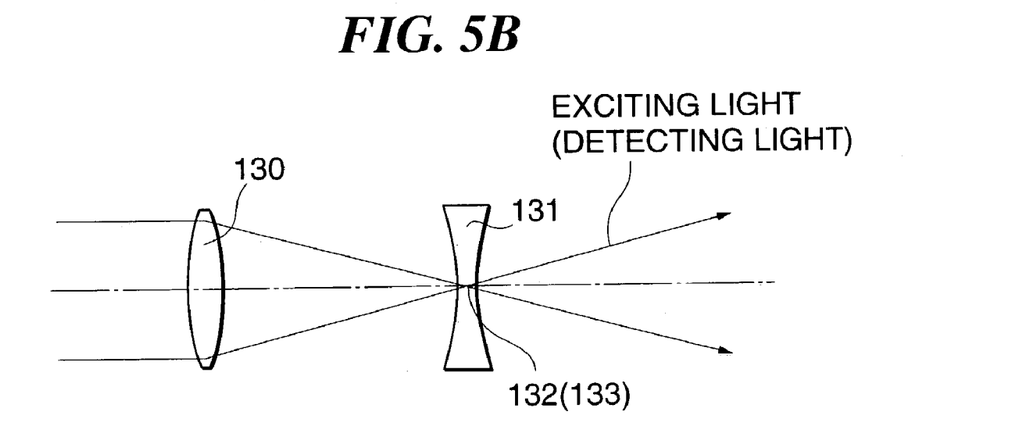
FIG. 5B is a view useful in explaining the formation position of the thermal lens formed by the exciting light and the focal position of the detecting light in the case that the objective lens does not have chromatic aberration.

In most cases of using the photothermal conversion spectroscopic analysis that makes use of a thermal lens, it is necessary for the focal position of the exciting light and the focal position of the detecting light to be different to one another. FIG. 5A is a view useful in explaining the formation position of the thermal lens formed by the exciting light and the focal position of the detecting light in the case that the objective lens has chromatic aberration. FIG. 5B is a view useful in explaining the formation position of the thermal lens formed by the exciting light and the focal position of the detecting light in the case that the objective lens does not have chromatic aberration. In FIGS. 5A and 5B the exciting light and the detecting light have different wavelengths to one another.

In the case that the objective lens 130 has chromatic aberration, as shown in FIG. 5A, the thermal lens 131 is formed at the focal position 132 of the exciting light, and the focal position 133 of the detecting light is shifted by an amount ΔL from the focal position 132 of the exciting light due to the difference in wavelength between the exciting light and the detecting light; the detecting light is thus refracted by the thermal lens 131 and hence changes in the refractive index of the thermal lens 131 can be detected as changes in the focal distance of the detecting light. On the other hand, in the case that the objective lens 130 does not have chromatic aberration, as shown in FIG. 5B, the focal position 133 of the detecting light is almost exactly the same as position of the thermal lens 131, which is formed at the focal position 132 of the exciting light; the detecting light is thus not refracted by the thermal lens 131, and hence changes in the refractive index of the thermal lens 131 cannot be detected.

Figure 6A:
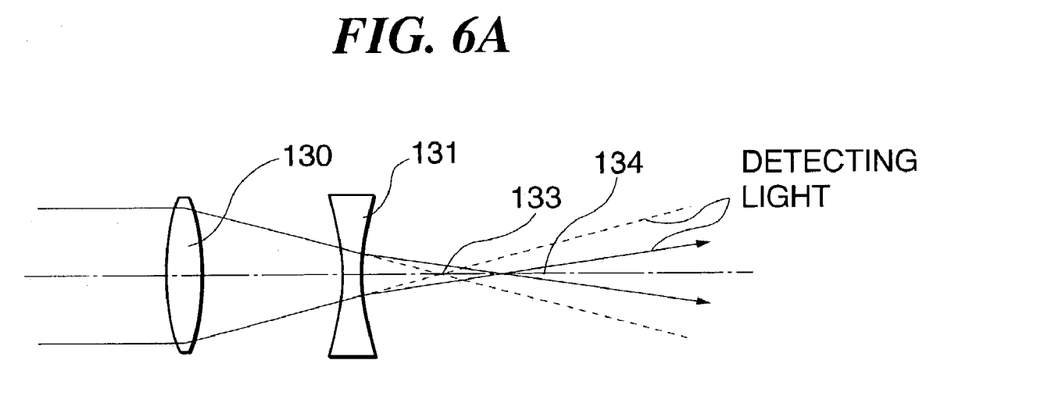
FIG. 6A is a view useful in explaining a method of detecting changes in refractive index within a thermal lens in a conventional photothermal conversion spectroscopic analysis apparatus, and shows a case in which the formation position of the thermal lens formed by the exciting light is made to be on the side of the focal position of the detecting light toward the objective lens.
Figure 6B:
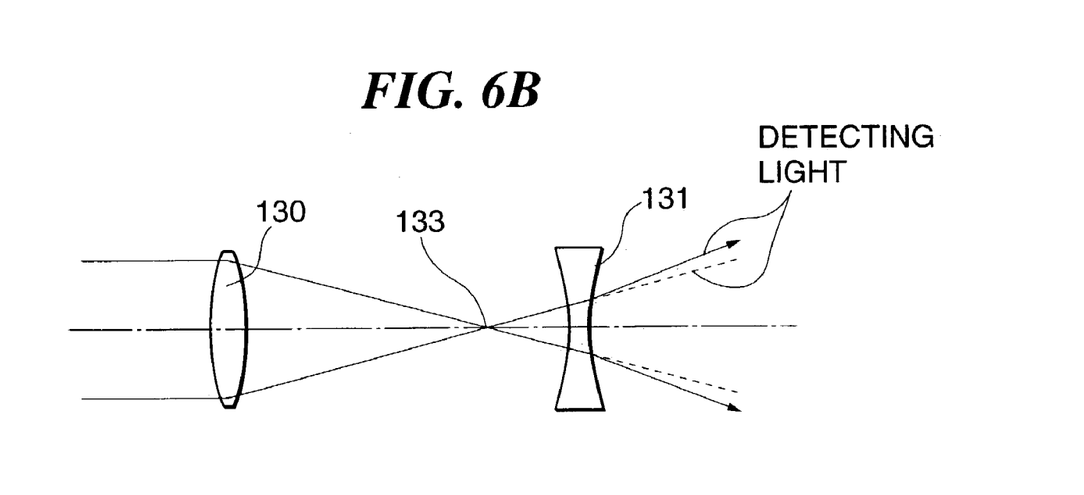
FIG. 6B is a view useful in explaining a method of detecting changes in refractive index within a thermal lens in a conventional photothermal conversion spectroscopic analysis apparatus, and shows a case in which the formation position of the thermal lens formed by the exciting light is made to be on the side of the focal position of the detecting light away from the objective lens.
Figure 7:
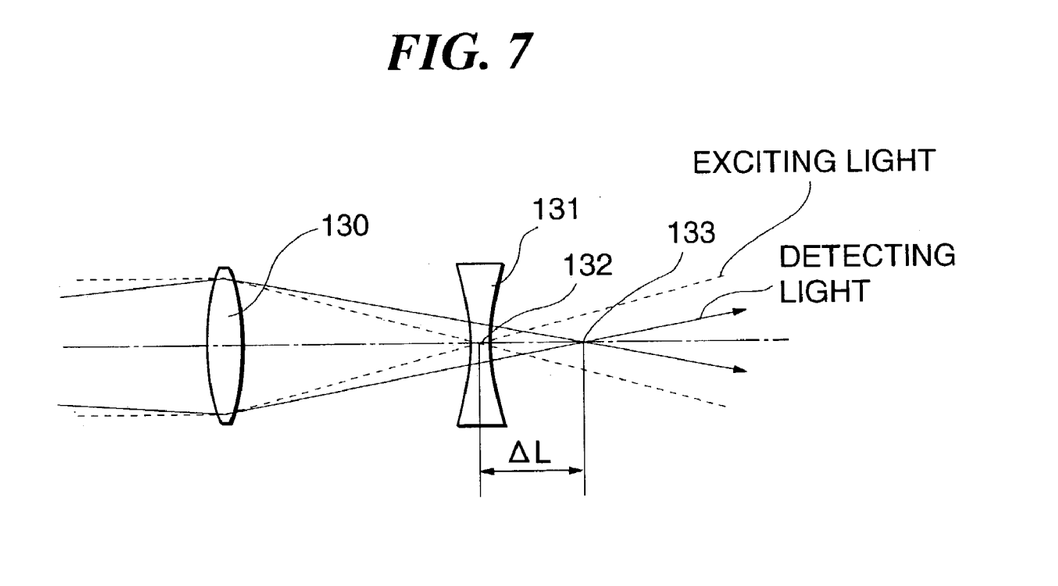
FIG. 7 is a view useful in explaining a method of detecting changes in refractive index within a thermal lens in a conventional photothermal conversion spectroscopic analysis apparatus, and shows a case in which the detecting light is diverged using a concave lens inserted into the optical path of the detecting light, whereby the focal position of the detecting light is made to be more distant than the focal position of the exciting light.

However, the objective lens of a microscope is generally manufactured so as not to have chromatic aberration, and hence the focal position 133 of the detecting light is almost exactly the same as the focal position 132 of the exciting light, i.e. the position of the center of the thermal lens 131, as described above (FIG. 5B). Changes in the refractive index of the thermal lens 131 thus cannot be detected. There has thus been a problem that every time measurement is carried out, trouble must be taken to either shift the position of formation of the thermal lens from the focal position 133 of the detecting light as shown in FIG. 6A or 6B, or else diverge or converge the detecting light slightly using a lens (not shown) before passing the detecting light through the objective lens so that the focal position 133 of the detecting light is shifted from the thermal lens 131 as shown in FIG. 7.

SUMMARY OF THE INVENTION

It is an object of the present invention to provide a photothermal conversion spectroscopic analysis method that enables high-sensitivity analysis to be carried out, and a photothermal conversion spectroscopic analysis apparatus that is compact in size and is able to implement the photothermal conversion spectroscopic analysis method.

To attain the above object, the present invention provides a photothermal conversion spectroscopic analysis method for analyzing a sample using detecting light that has passed through a thermal lens produced in the sample, the method comprising a convergent irradiation step of convergently irradiating exciting light and the detecting light onto the sample using a converging lens, and an analysis step of analyzing the sample using a change in intensity of the detecting light due to refraction upon passing through the thermal lens produced through the convergent irradiation of the exciting light, wherein a molar absorption coefficient of the sample at a wavelength of the exciting light is a predetermined number of times greater than a molar absorption coefficient of the sample at a wavelength of the detecting light.

According to this method, the molar absorption coefficient of the sample at the wavelength (frequency) of the exciting light is a predetermined number of times greater than the molar absorption coefficient of the sample at the wavelength (frequency) of the detecting light. As a result, the ratio (S/B) of the thermal lens signal intensity for the sample to the thermal lens signal intensity for the solvent in which the sample is dissolved, and the ratio (S/N) of the thermal lens signal intensity for the sample to noise, are high, and hence high-sensitivity photothermal conversion spectroscopic analysis becomes possible.

Preferably, the molar absorption coefficient of the sample at the wavelength of the exciting light is not less than 5 times the molar absorption coefficient of the sample at the wavelength of the detecting light.

As a result, because the molar absorption coefficient of the sample at the wavelength of the exciting light is not less than 5 times the molar absorption coefficient of the sample at the wavelength of the detecting light, S/B and S/N are adequately high, and hence it becomes possible to reliably realize high-sensitivity analysis.

More preferably, the molar absorption coefficient of the sample at the wavelength of the exciting light is not less than 10 times the molar absorption coefficient of the sample at the wavelength of the detecting light.

As a result, because the molar absorption coefficient of the sample at the wavelength of the exciting light is not less than 10 times the molar absorption coefficient of the sample at the wavelength of the detecting light, S/B and S/N are yet higher, and hence analysis with yet higher sensitivity becomes possible.

To attain the above object, the present invention provides a photothermal conversion spectroscopic analysis apparatus that analyzes a sample using detecting light that has passed through a thermal lens produced in the sample, the apparatus comprising an exciting light source that emits exciting light for exciting the sample to produce the thermal lens, a detecting light source that emits the detecting light that is passed through the thermal lens, a converging lens that converges the exciting light and irradiates the exciting light onto the sample, and also converges the detecting light so that the detecting light passes through the thermal lens, and an analyzer that analyzes the sample using a change in intensity of the detecting light due to refraction upon passing through the thermal lens, wherein a molar absorption coefficient of the sample at a wavelength of the exciting light is a predetermined number of times greater than a molar absorption coefficient of the sample at a wavelength of the detecting light.

According to this apparatus, the molar absorption coefficient of the sample at the wavelength of the exciting light is a predetermined number of times greater than the molar absorption coefficient of the sample at the wavelength of the detecting light. As a result, the ratio (S/B) of the thermal lens signal intensity for the sample to the thermal lens signal intensity for the solvent in which the sample is dissolved, and the ratio (S/N) of the thermal lens signal intensity for the sample to noise, are high, and hence high-sensitivity photothermal conversion spectroscopic analysis becomes possible.

Preferably, in the photothermal conversion spectroscopic analysis apparatus according to the present invention, the molar absorption coefficient of the sample at the wavelength of the exciting light is not less than 5 times the molar absorption coefficient of the sample at the wavelength of the detecting light.

As a result, because the molar absorption coefficient of the sample at the wavelength of the exciting light is not less than 5 times the molar absorption coefficient of the sample at the wavelength of the detecting light, S/B and S/N are adequately high, and hence analysis with higher sensitivity becomes possible.

More preferably, in the photothermal conversion spectroscopic analysis apparatus according to the present invention, the molar absorption coefficient of the sample at the wavelength of the exciting light is not less than 10 times the molar absorption coefficient of the sample at the wavelength of the detecting light.

As a result, because the molar absorption coefficient of the sample at the wavelength of the exciting light is not less than 10 times the molar absorption coefficient of the sample at the wavelength of the detecting light, S/B and S/N are yet higher, and hence analysis with yet higher sensitivity becomes possible.

Also preferably, the converging lens is a gradient refractive index lens.

As a result, because the converging lens is a gradient refractive index lens, the converging lens can be made smaller in size, and hence the apparatus as a whole can be made more compact in size.

More preferably, the gradient refractive index lens is a rod lens.

As a result, because the converging lens is a gradient index rod lens, the converging lens can be made yet smaller in size, and hence the apparatus as a whole can be made yet more compact in size, and moreover optical axis alignment becomes easy.

Also preferably, the photothermal conversion spectroscopic analysis apparatus comprises an optical fiber that guides the exciting light from the exciting light source to the converging lens and guides the detecting light from the detecting light source to the converging lens.

As a result, because an optical fiber is used to guide the exciting light and the detecting light, the optical axes of the exciting light and the detecting light are always coaxial with one another. Consequently, the need to mutually adjust the optical axes of the exciting light and the detecting light is eliminated, and hence the work efficiency of a user can be improved, and moreover jigs for adjusting the optical axes become unnecessary, and hence the apparatus can be made yet more compact in size.

More preferably, the converging lens is fixed to an end of the optical fiber that is a leading end in a direction of travel of the exciting light and the detecting light.

As a result, because the converging lens is fixed to the end of the optical fiber that is the leading end in the direction of travel of the exciting light and the detecting light, the optical axes of the exciting light, the detecting light and the converging lens are always coaxial with one another. Consequently, the need to mutually adjust the optical axes of the exciting light, the detecting light, and the converging lens is eliminated reliably, and hence the work efficiency of a user can be improved reliably.

Also more preferably, the optical fiber has a characteristic of propagating the exciting light and the detecting light in a single mode.

As a result, because the optical fiber propagates the exciting light and the detecting light in a single mode, the thermal lens produced by the exciting light has little aberration, and hence analysis can be carried out with yet higher sensitivity.

The above and other objects, features, and advantages of the invention will become more apparent from the following detailed description taken in conjunction with the accompanying drawings.

DETAILED DESCRIPTION OF THE PREFERRED EMBODIMENTS

A photothermal conversion spectroscopic analysis method, and a photothermal conversion spectroscopic analysis apparatus that carries out the method, according to an embodiment of the present invention will now be described in detail with reference to the drawings. It should be noted, however, that the present invention is not limited to this embodiment.

Figure 1:
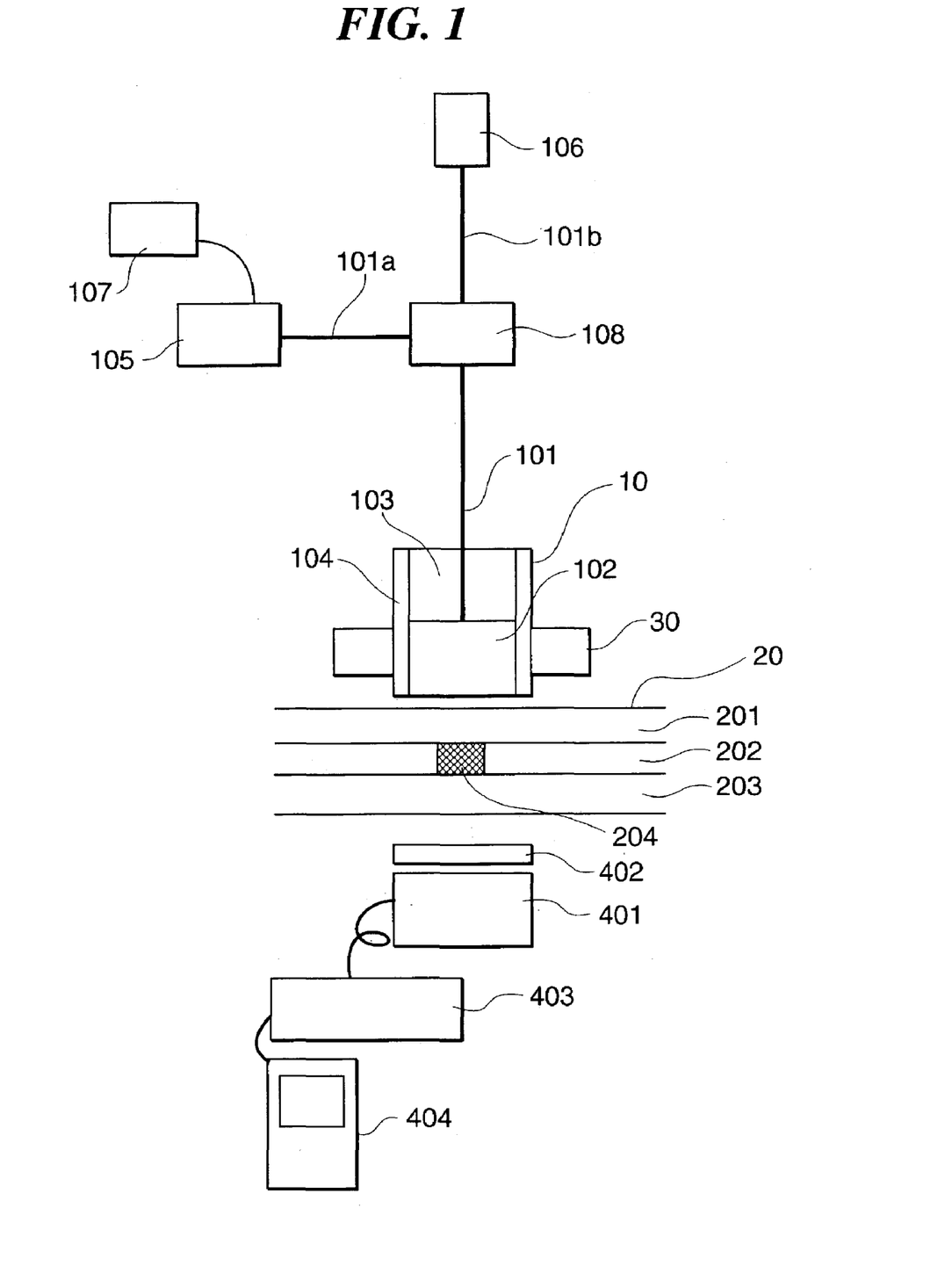
FIG. 1 is a schematic view showing the construction of a photothermal conversion spectroscopic analysis apparatus according to an embodiment of the present invention.

FIG. 1 is a schematic view showing the construction of a photothermal conversion spectroscopic analysis apparatus according to an embodiment of the present invention.

In FIG. 1, the photothermal conversion spectroscopic analysis apparatus according to the present embodiment has a lens unit 10 having a gradient index rod lens 102 (converging lens) built therein. An optical fiber 101 that propagates exciting light and detecting light, described below, in a single mode is inserted into the lens unit 10 from a side of incidence of the exciting light and the detecting light (i.e. from above in FIG. 1). The optical fiber 101 is a single-mode optical fiber that has only a single propagation mode, and thean end thereof that is inserted into the lens unit 10 is connected to one end face of the gradient index rod lens 102. The gradient index rod lens 102 converges the exciting light and irradiates the converged exciting light onto a sample to form a thermal lens, described below, and moreover converges the detecting light so that the detecting light passes through the thermal lens.

To expand out the outside diameter of the optical fiber 101 to be substantially the same as the outside diameter of the gradient index rod lens 102, a ferrule 103 having an outside diameter the same as the outside diameter of the gradient index rod lens 102 is disposed in series with the gradient index rod lens 102, and a leading end of the optical fiber 101 is passed through the center of the ferrule 103. The optical fiber 101 is fixed in position by the ferrule 103, and the gradient index rod lens 102 and the ferrule 103 are fixed in position by a sleeve 104. Here, the optical fiber 101 and the gradient index rod lens 102 may be made to be in close contact with one another, or a gap may be provided therebetween. The lens unit 10 constructed in this way is fixed using a jig 30 in a position such that the light exiting from the gradient index rod lens 102 is incident on a channel-formed plate-shaped member 20, described below.

The gradient index rod lens 102 has a transparent cylindrical body made, for example, of glass or plastic, and is such that the refractive index changes continuously from the center thereof toward the periphery thereof (see, for example, Japanese Examined Patent Application Publication (Kokoku) No. 63-63502). Such a lens is known as a converging light-transmitting body for which the refractive index n(r) at a position a distance r in the radial direction from the central axis is given approximately by a quadratic equation in r, $n(r) = n_0\{1-(g^2/2) \cdot r^2\}$, wherein $n_0$ represents the refractive index at the central axis, and g represents a quadratic distribution constant.

If the length $z_0$ of the gradient index rod lens 102 is chosen to be in a range of $0 < z_0 < \pi/2g$, then even though the gradient index rod lens 102 has flat end faces, the gradient index rod lens 102 will exhibit the same image formation characteristics as an ordinary convex lens; when a parallel light beam is incident on the gradient index rod lens 102, a focal point will be formed at a position a distance $s_o$ from the end face of the gradient index rod lens 102 from which the light beam exits, where $s_0 = \cot(gz_0)/n_0 g$.

Such a gradient index rod lens 102 may be manufactured, for example, using the following method.

A rod is first formed from a glass having as principal components thereof 57 to 63 mol % of $SiO_2$, 17 to 23 mol % of $B_2O_3$, 5 to 17 mol % of $Na_2O$, and 3 to 15 mol % of $Tl_2O$. The glass rod is then treated in an ion exchange medium such as potassium nitrate, thus carrying out ion exchange between thallium ions and sodium ions in the glass and potassium ions in the medium, and hence producing a refractive index distribution in the glass rod in which the refractive index decreases continuously from the center of the glass rod outward in the radial direction.

Because the end faces of the gradient index rod lens 102 are flat, the optical fiber 101 can easily be installed, and moreover the optical axis of the gradient index rod lens 102 and the optical axis of the optical fiber 101 can easily be aligned with one another. Moreover, because the gradient index rod lens 102 is a solid-cylindrical body, the lens unit 10 as a whole can also easily be made to be solid-cylindrical. As a result, holding the lens unit 10 using the jig 30 is extremely easy. Furthermore, because the gradient index rod lens 102 is considerably smaller in size than a microscope objective lens, the apparatus as a whole can be made more compact in size.

The reason for making the optical fiber 101 be a single-mode optical fiber is that when detecting a very small amount of a solute in a sample using the photothermal conversion spectroscopic analysis method, it is preferable to narrow down the exciting light as much as possible, and hence increase the energy used in the photothermal conversion, and moreover make there be little aberration in the thermal lens produced by the exciting light.

The exciting light used for producing the thermal lens preferably has a Gaussian distribution. The light exiting from the single-mode optical fiber 101 will always have a Gaussian distribution, and hence the focal point of the exciting light can be made to be small in size. Moreover, in the case that the thermal lens produced by the exciting light is small in size, to make the amount of the detecting light that passes through the thermal lens be as high as possible, it is preferable to also narrow down the detecting light as much as possible. From this standpoint as well, it is preferable for the optical fiber to propagate the exciting light and the detecting light in a single mode.

Any type of optical fiber that will transmit the exciting light and the detecting light can be used as the optical fiber 101, but in the case that a multi-mode optical fiber is used, the light emitted from the optical fiber will not have a Gaussian distribution, and moreover the emitted light pattern will vary according to various conditions such as the state of curvature of the optical fiber 101, and hence it will not necessarily be possible to obtain stable exiting light. It is thus preferable for the optical fiber 101 to be a single-mode optical fiber as described above.

In the vicinity of an end of the optical fiber 101 that is opposite to the end thereof that is inserted into the lens unit 10 are provided an exciting light source 105 that outputs the exciting light for exciting the sample, a detecting light source 106 that outputs the detecting light that is made to pass through the thermal lens to analyze the sample, a modulator 107 for modulating the exciting light, and a two-wavelength multiplexing element 108 for multiplexing the exciting light and the detecting light; the exciting light is led from the exciting light source 105 to the two-wavelength multiplexing element 108 by an optical fiber 101a, and the detecting light is led from the detecting light source 106 to the two-wavelength multiplexing element 108 by an optical fiber 101b. Note that instead of using the two-wavelength multiplexing element 108, the exciting light and the detecting light may be made to be coaxial with one another using a dichroic mirror or the like before being led into the optical fiber 101.

The exciting light and detecting light that have been multiplexed by the two-wavelength multiplexing element 108 propagate through the optical fiber 101, enter the lens unit 10, exit from the gradient index rod lens 102, and are incident on the channel-formed plate-shaped member 20. The channel-formed plate-shaped member 20 is comprised of three glass substrates 201, 202 and 203 bonded on top of one another. A channel 204 is formed in the glass substrate 202, for carrying out mixing, agitation, synthesis, separation, extraction, detection or the like on the sample.

From the perspective of durability and chemical resistance, the channel-formed plate-shaped member 20 is preferably made of a glass, and moreover, considering the case of handling biological samples such as cell samples, for example the case of carrying out DNA analysis, it is preferable to use a glass having high acid resistance and alkali resistance, specifically a borosilicate glass, a soda lime glass, an aluminoborosilicate glass, a quartz glass or the like. However, if the usage is limited accordingly, then an organic substance such as a plastic can be used instead.

The glass substrates 201, 202 and 203 may be bonded together using an adhesive, for example an organic adhesive such as an acrylic adhesive or an epoxy adhesive, or an inorganic adhesive; the adhesive may be, for example, an ultraviolet-curing type, a thermosetting type, or a two-part type (in which curing takes place when two liquid parts are mixed together). Alternatively, the glass substrates 201, 202 and 203 may be fused together by heat fusion.

A photoelectric converter 401 for detecting the detecting light is provided at a location facing the lens unit 10 such that the channel-formed plate-shaped member 20 is between the lens unit 10 and the photoelectric converter 401 and such that the photoelectric converter 401 faces onto the channel 204, and a wavelength filter 402 that selectively transmits only the detecting light out of the exciting light and the detecting light is provided between the channel-formed plate-shaped member 20 and the photoelectric converter 401. Moreover, so that only part of the detecting light is selectively transmitted, a member having a pinhole formed therein may be additionally provided in the optical path of the detecting light at a location upstream from the photoelectric converter 401. Signals obtained by the photoelectric converter 401 are sent to a lock-in amplifier 403 for carrying out synchronization with the modulator 107 used for modulating the exciting light, and are then analyzed by a computer 404, whereby the sample is analyzed.

According to the photothermal conversion spectroscopic analysis apparatus of the present embodiment, a gradient index rod lens 102 is installed at the leading end of an optical fiber 101 that propagates the exciting light and the detecting light. As a result, there is no need to adjust the optical axes of the exciting light, the detecting light, and the gradient index rod lens 102 for each measurement, and moreover jigs for aligning the optical axes and a sturdy baseplate are unnecessary, and hence the work efficiency of a user can be improved, and furthermore the photothermal conversion spectroscopic analysis apparatus can be made more compact in size.

The focal position of the exciting light focussed by the gradient index rod lens 102 must be in the channel 204 of the channel-formed plate-shaped member 20. The gradient index rod lens 102 does not have to be in contact with the channel-formed plate-shaped member 20, but in the case that the gradient index rod lens 102 is made to be in contact with the channel-formed plate-shaped member 20, the focal position of the gradient index rod lens 102 can be adjusted through the thickness of the upper glass substrate 201 of the channel-formed plate-shaped member 20. In the case that the thickness of the upper glass substrate 201 is insufficient, a spacer for adjusting the focal position of the gradient index rod lens 102 may be inserted between the gradient index rod lens 102 and the upper glass substrate 201. In the case that the focal position of the exciting light is fixed in advance to be in the channel 204 of the channel-formed plate-shaped member 20 in this way, subsequent adjustment of the focal position becomes unnecessary, and hence the photothermal conversion spectroscopic analysis apparatus can be made yet more compact in size.

The gradient index rod lens 102 is set such that the focal position of the detecting light is shifted slightly by an amount $\Delta L$ relative to the focal position of the exciting light due to chromatic aberration (see FIG. 5A).

The confocal length Ic (nm) is given by $Ic = \pi \cdot (d/2)^2 / \lambda_1$, wherein d represents the Airy disk and is given by $d = 1.22 \times \lambda_1 / NA$, $\lambda_1$ represents the wavelength (nm) of the exciting light, and NA represents the numerical aperture of the gradient index rod lens 102. In the case of using an optical fiber, the numerical aperture of the light exiting from the optical fiber is small, and hence if a gradient index rod lens 102 having a large numerical aperture is used, then it is necessary to use the numerical aperture of the optical fiber instead of the numerical aperture of the gradient index rod lens 102 in the calculation.

The amount $\Delta L$ described above varies according to the thickness of the sample on which measurements are to be carried out. When carrying out measurements on a sample having a thickness lower than the confocal length, it is most preferable for the amount $\Delta L$ to be equal to $\sqrt{3} \times Ic$.

The amount $\Delta L$ represents the absolute value of the difference between the focal position of the detecting light and the focal position of the exciting light, and hence the result is the same regardless of whether the focal distance of the detecting light is longer or shorter than the focal distance of the exciting light.

If the leading end of the optical fiber 101 were made into a spherical shape or the like and this were made to be the lens, then it would be possible to narrow down the exciting light and the detecting light without installing a separate lens at the leading end of the optical fiber 101. However, in this case, there would be hardly any chromatic aberration, and hence the focal positions of the exciting light and the detecting light would almost coincide with one another. There would thus be a problem of the thermal lens signal being hardly detectable. Moreover, if the leading end of the optical fiber 101 were made into the lens, then this lens would have high comatic aberration, and hence there would also be a problem of the focal points of the exciting light and the detecting light being too large. In the present embodiment, a separate gradient index rod lens 102 is thus installed at the leading end of the optical fiber 101.

In the present embodiment, a gradient index rod lens 102 is used, but there is no such limitation; any lens having the desired chromatic aberration can be used.

At present, integration technology for carrying out chemical reactions in very small spaces is attracting attention in view of the rapidity of chemical reactions, and the need to carry out reactions using very small amounts, on-site analysis and so on, and research into this technology is being carried out with vigor throughout the world.

As one example of such chemical reaction integration technology, there are apparatuses for carrying out any of mixing, reaction, separation, extraction, and detection on a liquid-borne sample in a very fine channel formed in a small glass substrate or the like. Such an apparatus may be used with a single function, for example for only separation, or may be used with a combination of functions.

As an example of an apparatus for only separation out of the above functions, an electrophoresis apparatus for analyzing extremely small amounts of proteins, nucleic acids or the like has been proposed; this apparatus has a channel-formed plate-shaped member comprised of two glass substrates joined together (see, for example, Japanese Laid-open Patent Publication (Kokai) No. 8-178897).

The channel formed in the channel-formed plate-shaped member used in such an apparatus generally has a depth of approximately 50 to 100 µm, this being to enable the sample solution to flow while maintaining the liquid properties thereof. Because photothermal conversion spectroscopic analysis is implemented in such a state in which the sample solution is flowing through the channel, the amount of the sample analyzed is extremely small, and hence the analysis must be carried out with extremely high sensitivity.

In the photothermal conversion spectroscopic analysis, the exciting light can also be used as the detecting light, but the sensitivity is improved if exciting light and detecting light of different wavelengths to one another are used. Consequently, for measurement in a fine channel as described above, it is preferable for the exciting light and the detecting light to have different wavelengths to one another.

A description will now be given of how the wavelengths of the exciting light and the detecting light should be selected to enable high-sensitivity photothermal conversion spectroscopic analysis to be carried out. The higher the amount of absorption of the exciting light by the substance that absorbs the exciting light, the higher the amount of conversion into thermal energy, and hence the larger the thermal lens effect, and thus the higher the sensitivity of the photothermal conversion spectroscopic analysis. The wavelength of the exciting light is thus selected from wavelengths that can be absorbed by the sample. On the other hand, the detecting light is used for measuring the power of the thermal lens formed by the exciting light, and hence it is preferable for the detecting light to not contribute to the formation of the thermal lens. It is thus preferable for the wavelength of the detecting light to be selected from wavelengths at which there is little absorption by the sample.

However, some substances absorb light over a broad wavelength range. In the case of such a substance, considering also absorption by the solvent, it may be difficult to select for the detecting light a wavelength at which the sample does not absorb. Moreover, if only a single substance is detected by a particular apparatus, then it will be relatively easy to satisfy the above conditions. However, in the case of trying to carry out detection of a variety of substances having different absorption spectra to one another using an apparatus in which the wavelengths of the exciting light and the detecting light cannot be changed, it will be difficult to make the above conditions be satisfied for all of the samples.

The present inventors discovered that if the wavelengths of the exciting light and the detecting light are selected such that the molar absorption coefficient of a sample at the wavelength of the exciting light is not less than 5 times the molar absorption coefficient of the sample at the wavelength of the detecting light, then photothermal conversion spectroscopic analysis using a thermal lens effect can be carried out with high sensitivity. Moreover, the present inventors discovered that if the wavelengths of the exciting light and the detecting light are selected such that the molar absorption coefficient of a sample at the wavelength of the exciting light is not less than 10 times the molar absorption coefficient of the sample at the wavelength of the detecting light, then the sensitivity of measurement can be further improved. By maintaining such a relationship between the molar absorption coefficient at the wavelength of the exciting light and the molar absorption coefficient at the wavelength of the detecting light, measurement can be carried out on a large number of substances with high sensitivity using a single apparatus in which the wavelengths of the exciting light and the detecting light cannot be changed.

Figure 2:
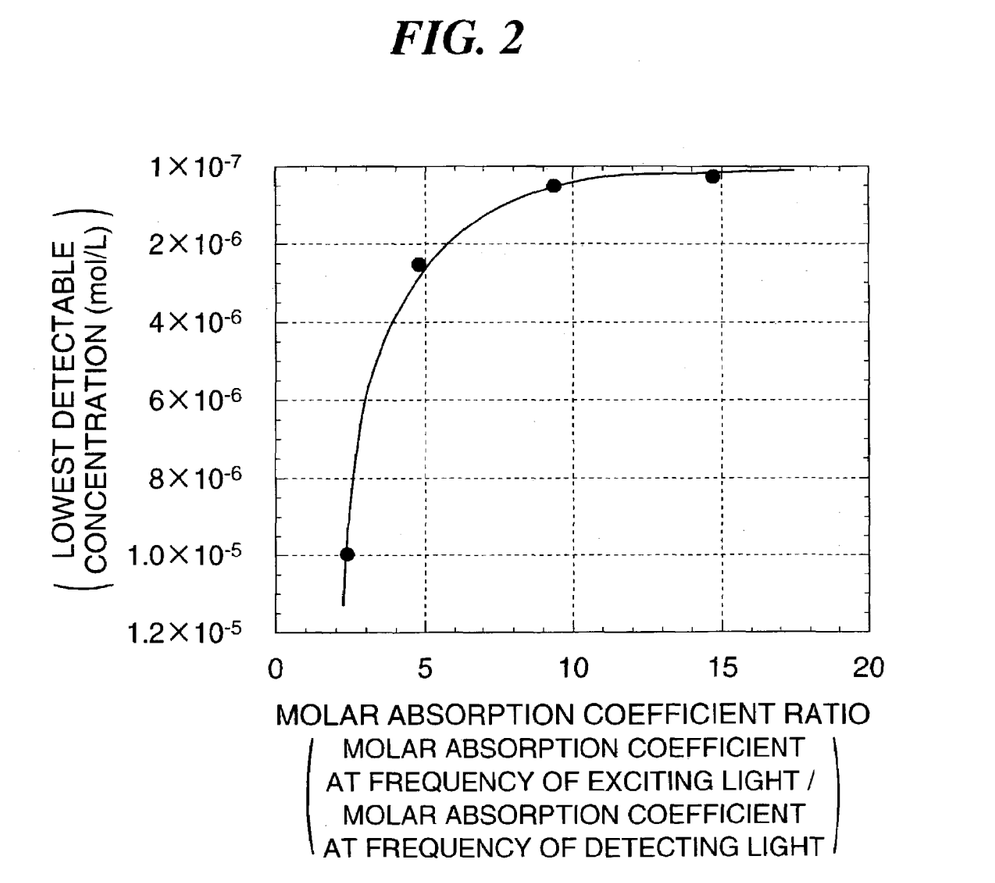
FIG. 2 is a graph showing the relationship between a molar absorption coefficient ratio of a sample and sensitivity.
Figure 3:
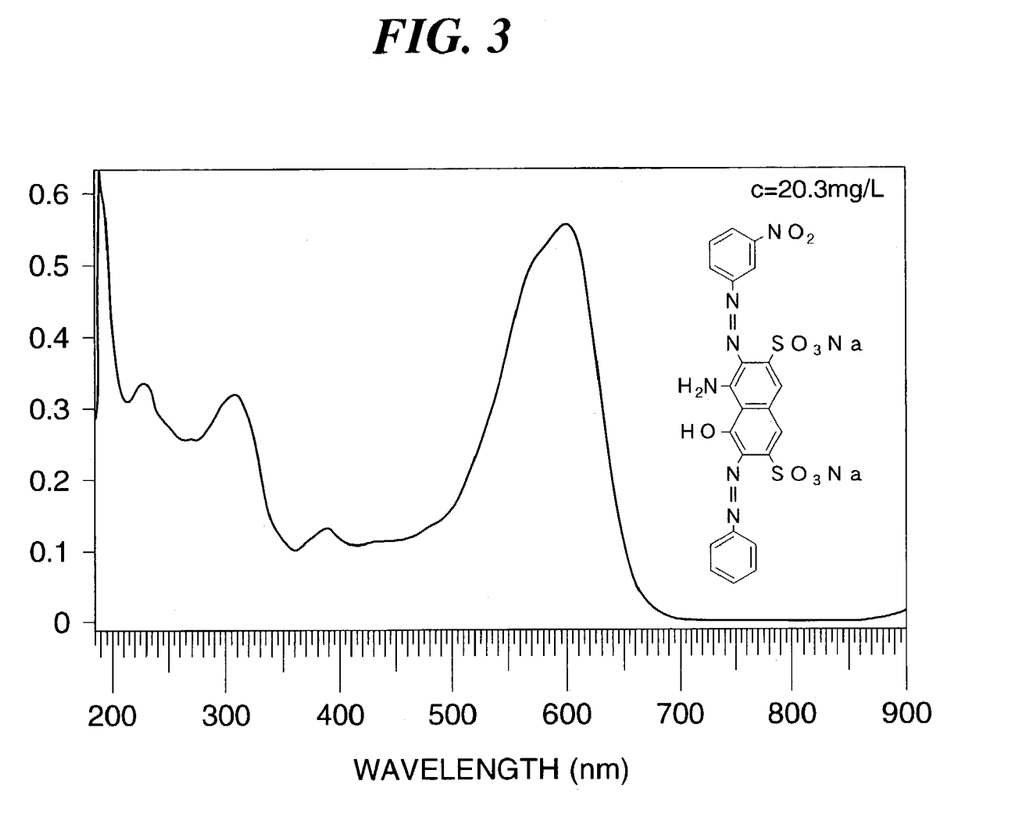
FIG. 3 is a graph showing the absorption spectrum of the sample.

FIG. 2 is a graph showing the relationship between the molar absorption coefficient ratio of a sample, which is the ratio of the molar absorption coefficient of the sample at the wavelength of the exciting light to the molar absorption coefficient of the sample at the wavelength of the detecting light, and sensitivity. FIG. 3 is a graph showing the absorption spectrum of the sample.

FIG. 2 shows an example of how the sensitivity of photothermal conversion spectroscopic analysis using a thermal lens changes in the case of changing the ratio of the molar absorption coefficient at the wavelength of the exciting light to the molar absorption coefficient at the wavelength of the detecting light. The measurements for this example were taken under the following conditions.

Acid Blue 29 (CAS No. 5850-35-1), which has a peak absorption wavelength of 602 nm and a molar absorption coefficient of approximately 17,000 at this wavelength, was used as the sample.

The sample for which the absorption spectrum is shown in FIG. 3 is Acid Blue 29. Aqueous solutions containing various concentrations of Acid Blue 29 were prepared, and for each of the aqueous solutions the intensity of detecting light of a predetermined wavelength that had passed through a thermal lens produced in the aqueous solution (the thermal lens signal intensity) was measured as a first detecting light intensity, and the intensity of detecting light of the predetermined wavelength that had been passed through water (i.e. a blank) was measured as a second detecting light intensity. Then, the measured first detecting light intensity was compared with the measured second detecting light intensity that contains noise. The minimum concentration at which the first detecting light intensity and the second light intensity can be clearly distinguished from each other was taken to be the lowest detectable concentration for detecting light of that wavelength.

This procedure was repeated for different wavelengths, and the lowest detectable concentration was determined for each wavelength.

An SLH lens as listed in the SELFOC lens catalog of Nippon Sheet Glass Co., Ltd. was used as the objective lens. An optical fiber capable of transmitting light of wavelength 500 nm and above in a single mode was fixed to this lens, and exciting light of wavelength 635 nm and detecting light of any of various wavelengths were led into the optical fiber after having been made coaxial using a dichroic mirror. An aqueous solution of Acid Blue 29 of any of various concentrations was put into a 0.1 mm-deep channel 204 of a channel-formed plate-shaped member 20, and this was used as a cell. An ND filter was inserted into the optical path of the detecting light, thus adjusting the intensity of the detecting light to be the same for all of the wavelengths. The intensities of the exciting light and the detecting light during the measurements were 3.5 mW for the exciting light and 0.25 mW for the detecting light at the position of exiting the SELFOC lens.

According to FIG. 2, if the molar absorption coefficient of the Acid Blue 29 at the wavelength of the exciting light is not less than 5 times the molar absorption coefficient of the Acid Blue 29 at the wavelength of the detecting light, then the lowest detectable concentration is not more than $2.5 \times 10^{-6}$ mol/l, and if the molar absorption coefficient of the Acid Blue 29 at the wavelength of the exciting light is not less than 10 times the molar absorption coefficient of the Acid Blue 29 at the wavelength of the detecting light, then the lowest detectable concentration is not more than $5 \times 10^{-7}$ mol/l. Consequently, if the molar absorption at the wavelength of the exciting light is not less than 5 times the molar absorption at the wavelength of the detecting light, then the ratio (S/B) of the thermal lens signal intensity for the sample to the thermal lens signal intensity for the solvent, and the ratio (S/N) of the thermal lens signal intensity for the sample to noise, are high, and hence high-sensitivity photothermal conversion spectroscopic analysis becomes possible. Furthermore, if the molar absorption at the wavelength of the exciting light is not less than 10 times the molar absorption at the wavelength of the detecting light, then photothermal conversion spectroscopic analysis with yet higher sensitivity becomes possible.

According to the present embodiment, the wavelengths of the exciting light and the detecting light are selected such that a suitable relationship is satisfied as described above, and hence high-sensitivity measurement can be carried out. Moreover, a gradient index rod lens is used as the objective lens, and optical fibers are used in the optical system that guides the exciting light and the detecting light from the respective light sources to the gradient index rod lens; there is thus no shifting out of alignment of the optical axes, and hence there is no need to adjust the optical axes of the exciting light, the detecting light, and the gradient index rod lens for each measurement, and thus the work efficiency of a user can be improved. Moreover, there is no need to provide jigs for adjusting the optical axes, and hence the apparatus can be made more compact in size.

What is claimed is:

1. A photothermal conversion spectroscopic analysis method for analyzing a sample using detecting light that has passed through a thermal lens produced in the sample, the method comprising:
   a convergent irradiation step of convergently irradiating exciting light and the detecting light onto the sample using a converging lens; and
   an analysis step of analyzing the sample using a change in intensity of the detecting light due to refraction upon passing through the thermal lens produced through the convergent irradiation of the exciting light;
   wherein a molar absorption coefficient of the sample at a wavelength of the exciting light is not less than 5 times a molar absorption coefficient of the sample at a wavelength of the detecting light.

2. A photothermal conversion spectroscopic analysis method as claimed in claim 1, wherein the molar absorption coefficient of the sample at the wavelength of the exciting light is not less than 10 times the molar absorption coefficient of the sample at the wavelength of the detecting light.

3. A photothermal conversion spectroscopic analysis apparatus that analyzes a sample using detecting light that has passed through a thermal lens produced in the sample, the apparatus comprising:
   an exciting light source that emits exciting light for exciting the sample to produce the thermal lens;
   a detecting light source that emits the detecting light that is passed through the thermal lens;
   a converging lens that converges the exciting light and irradiates the exciting light onto the sample, and also converges the detecting light so that the detecting light passes through the thermal lens; and
   an analyzer that analyzes the sample using a change in intensity of the detecting light due to refraction upon passing through the thermal lens;
   wherein a molar absorption coefficient of the sample at a wavelength of the exciting light is not less than 5 times a molar absorption coefficient of the sample at a wavelength of the detecting light.

4. A photothermal conversion spectroscopic analysis apparatus as claimed in claim 3, wherein the molar absorption coefficient of the sample at the wavelength of the exciting light is not less than 10 times the molar absorption coefficient of the sample at the wavelength of the detecting light.

5. A photothermal conversion spectroscopic analysis apparatus as claimed in claim 3, wherein said converging lens is a gradient refractive index lens.

6. A photothermal conversion spectroscopic analysis apparatus as claimed in claim 5, wherein said gradient refractive index lens is a rod lens.

7. A photothermal conversion spectroscopic analysis apparatus as claimed in claim 3, further comprising an optical fiber that guides the exciting light from said exciting light source to said converging lens and guides the detecting light from said detecting light source to said converging lens.

8. A photothermal conversion spectroscopic analysis apparatus that analyzes a sample using detecting light that has passed through a thermal lens produced in the sample, the apparatus comprising:
   an exciting light source that emits exciting light for exciting the sample to produce the thermal lens;
   a detecting light source that emits the detecting light that is passed through the thermal lens;
   a converging lens that converges the exciting light and irradiates the exciting light onto the sample, and also converges the detecting light so that the detecting light passes through the thermal lens;
   an analyzer that analyzes the sample using a change in intensity of the detecting light due to refraction upon passing through the thermal lens; and
   an optical fiber that guides the exciting light from said exciting light source to said converging lens and guides the detecting light from said detecting light source to said converging lens;
   wherein a molar absorption coefficient of the sample at a wavelength of the exciting light is a predetermined number of times greater than a molar absorption coefficient of the sample at a wavelenqth of the detecting light; and
   wherein said converging lens is fixed to an end of said optical fiber that is a leading end in a direction of travel of the exciting light and the detecting light.

9. A photothermal conversion spectroscopic analysis apparatus as claimed in claim 7, wherein said optical fiber has a characteristic of propagating the exciting light and the detecting light in a single mode.

* * * * *